United States Patent [19]
Ojo-Amaize et al.

[11] Patent Number: 6,001,871
[45] Date of Patent: Dec. 14, 1999

[54] HYPOESTOXIDES, DERIVATIVES AND AGONISTS THEREOF FOR USE AS ANTIVIRAL AGENTS

[75] Inventors: Emmanuel A. Ojo-Amaize, Glendora, Calif.; Joseph I. Okogun, New Rochelle, N.Y.

[73] Assignee: Immune Modulation, Inc., Bloomington, Calif.

[21] Appl. No.: 09/007,308

[22] Filed: Jan. 15, 1998

[51] Int. Cl.[6] .................... A01N 43/20; C07D 303/00; C07D 303/06
[52] U.S. Cl. ............................ 514/475; 549/512; 549/544
[58] Field of Search ............................ 514/475; 549/512, 549/544

[56] References Cited

PUBLICATIONS

T. Mosmann; (1983) "Rapid Colorimetric Assay for Cellular Growth and Survival: Application to Proliferation and Cytotoxicity Assays" 65 *Journal of Immunological Methods*, 55–63.
Fahad A. Alrabiah and Stephen L. Sacks; (1996) "New Antiherpesvirus Agents Their Targets and Therapeutic Potential" Jul. 52 (1) *Drugs* 17–32.
Birgit Sköldenburg; (1996) "Herpes Simplex Encephalitis" 100 *Scand J. Infect Dis. Suppl* 8–13.
G.B. Elion; (1993) "Acyclovir: Discovery, Mechanism of Action, and Selectivity"1 *Journal of Medical Virology Supplement* 2–6.
Balkwill, F.R.; (1989) "Interferons" 1 *Lancet* 1060–1063.
Gadler, H.; (1983) "Nucleic Acid Hybridization for Measurement of Antiviral Compounds on Human Cytomegalvirus DNA Replication" 24 *Antimicrob. Agents Chemother* 370–374.
Hartman A.F.; (1997) "Prim Care" 24(3) 531–559.
Hayashi et al.; (1996) "Characterization of Antiviral Activity of Sesquitrepene, Triptofordin" 37 *J. Antimicrob. Chemotherap.* 759–768.
Japour et al.; (1993) "Antimicro Agents Chemotherapy" 37:1095–1101.
McDonald et al.; (1997) 157(9) "Arch. Intern. Med." 951–959.
Okogun et al.; (1982) "Roseanolone: A New Diterpene from Hypoestes Rosea" 37c *Z. Naturforsc.* 558–561.
Antona J. Wagstaff, et al.; (1994) "Aciclovir: A Reappraisal of its Antiviral Activity, Pharmacokinetic Properties and Therapeutic Efficacy" 47 (1) *Drugs* 153–204.
Balfour, H.H. Jr., 1999, "Drug Therapy: Antiviral Drugs," vol. 340 The New England Journal of Medicine, No. 16, pp. 1255–1268, Massachusetts Medical Society.

*Primary Examiner*—Russell Travers
*Attorney, Agent, or Firm*—Pillsbury Madison & Sutro LLP

[57] ABSTRACT

A method for inhibiting the growth of lentiviruses and Herpetoviridae viruses, including HIV-1 and HSV-1, -2, respectively, in subjects, comprising administering to a subject in need of antiviral therapy a pharmaceutical composition comprising a therapeutically effective amount of a compound of the formula

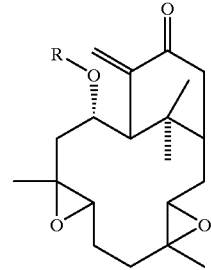

I where:

R is (i) H, $PO_3^=$, alkyl of 1 to 12 carbon atoms substituted or unsubstituted, straight chain or branched, 0 to 6 double bonds, $(CH_2)_n$morpholine where n=1–4, morpholinomethylphenyl, orthoaminophenyl, orthohydroxyphenyl, $(CH_2)_n COOR_2$ where n=1–4 where $R_2$ is H, an alkalai metal salt, an alkaline earth metal salt, $NH_4^=$, $N^+(R_3)_4$
where $R_3$ is independently selected from the group consisting of H and alkyl of 1 to 4 carbon atoms, or (ii) $COR_1$ wherein $R_1$ is selected from the group consisting of H, $(CH_2)_n CH_3$, where n=0–6, $(CH_2)_n COOR_2$ where n=1–4 and $R_2$ is previously defined, $(CH_2)_n N^+(R_3)_4$ wherein n=1–4, and $(CH_2)_n SO_3^-$ where n=1–4,
and pharmaceutically acceptable salts thereof.

8 Claims, 3 Drawing Sheets

Inhibitory Effect of JO-4A on HIV-1 Replication in Cultured
Human Peripheral Blood Mononuclear Cells Toxicity Testing of JO-4A on Cultured Normal Human PBMCs
by Trypan Blue dye-exclusion Test Figure 2A: Effect of JO-4 on HSV-1 replication
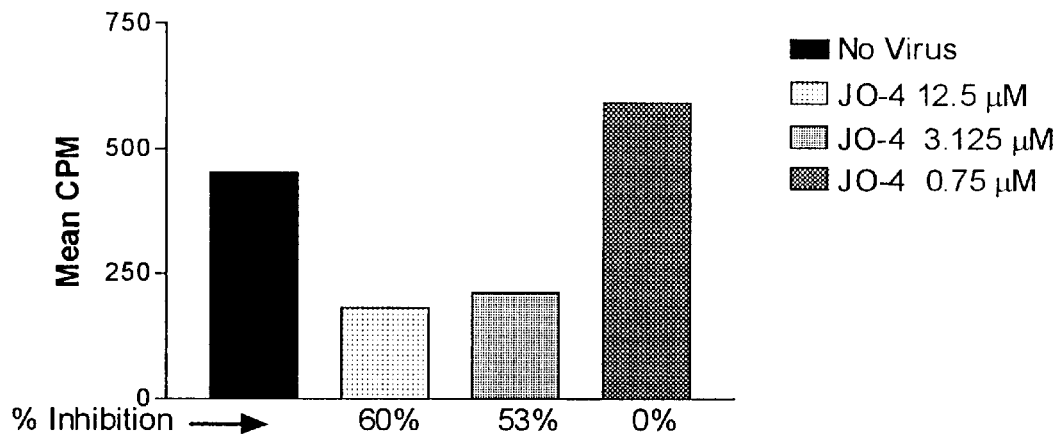
Figure 2B: Effect of JO-4 on HSV-2 replication
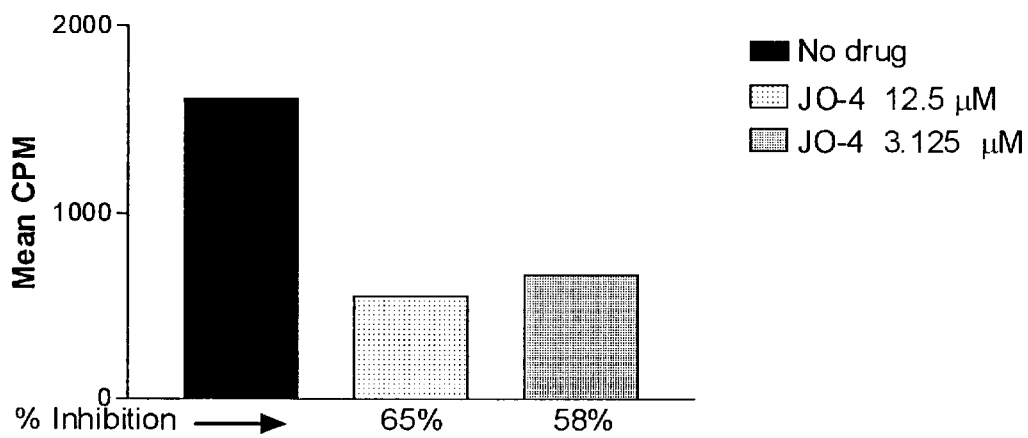
Figure 2C: Effect of JO-4A on HSV-2 replication
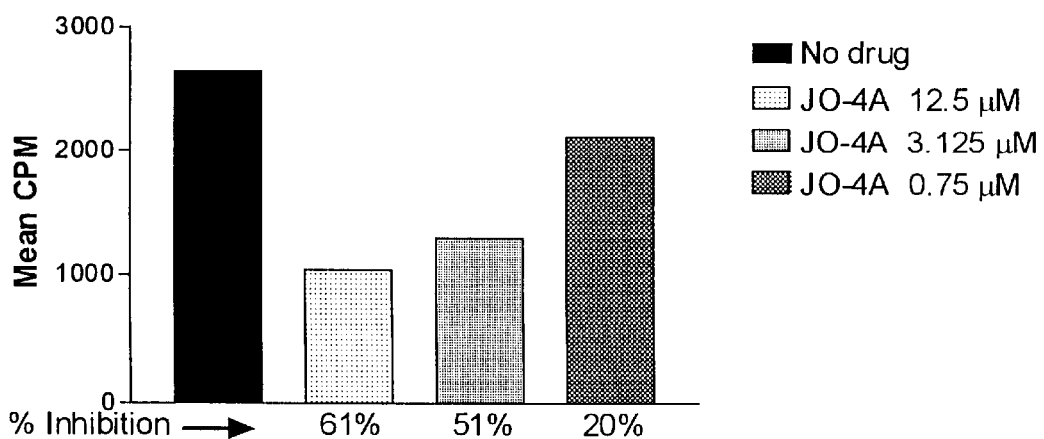

Effect of JO-4 on Normal Uninfected African Green Monkey Kidney Cells

Effect of JO-4A on Normal Uninfected African Green Monkey Kidney Cells

HYPOESTOXIDES, DERIVATIVES AND AGONISTS THEREOF FOR USE AS ANTIVIRAL AGENTS

BACKGROUND OF THE INVENTION

1. Field of the Invention

This invention relates to the use of diterpene compounds, in particular hypoestoxides, derivatives and agonists thereof for antiviral therapy.

2. Background Art

The interactions between viruses and the host immune system are not only complex and fascinating but also critical in determining the outcome of infection and strategies for its prevention. The goal of antiviral chemotherapy is to inhibit replication of the viral genome without affecting the DNA of the cell.

Of the large number of agents under development for the treatment of herpes virus infections [herpes simplex virus types 1 and 2 (HSV-1 and HSV-2), varicella zoster virus (VZV), cytomegalovirus (CMV), Epstein-Barr virus (EBV)], only ten have apparently reached clinical development (Alrabiah FA and Sacks, SL; Drugs 1996:52(1):17–32). Although aciclovir is the treatment of choice in herpes simplex encephalitis (HSV-1), mortality and morbidity remain problematic (Skoldenberg B; Scand. J. Infect Dis Suppl 100:8–13, 1996). The same can be said about interferon-alpha (IFN-α) and interferon-beta (IFN-β). Although both IFNs have considerable antiviral and immunomodulatory effects, their success as antiviral agents in humans has been hindered by their dose-limiting side effects (Balkwill, FR. Interferons; Lancet 1989;1:1060–1063). HSV-2 is the most common infective cause of genital ulceration in developed countries. Currently, 1 in 5 (20%) teenage adults in the United States is infected with genital herpes. A range of antiviral agents has become available since the early 1980s which can reduce disease severity, but HSV infection is life-long and, once established, there is no treatment which will eliminate it (Brugha, R. et al. Int. J. Epidemiol 1997;26:698–709). Therefore, there is a tremendous need to develop new approaches and agents to eliminate HSV infection.

The number of human immunodeficiency virus type 1 (HIV-1)-infected individuals is currently estimated at 1–2 million in the United States, with a worldwide incidence of approximately 20 million. By the year 2000, it is estimated that more than 3 million Americans will be infected with HIV-1.

Until recently, treatment of HIV-1 infection was limited to the use of nucleoside inhibitors of the viral enzyme reverse transcriptase (RTI). While these agents initially offered promise, they have only modest antiviral activity and the benefits of treatment are limited by the emergence of drug resistance and dose-limiting toxic effects (McDonald CK et al. Arch Intern Med 1997;157(9):951–959). Although treatment of HIV with nucleoside analog RTIs and protease inhibitors forms the backbone of anti-HIV therapy, non-nucleoside RTIs, immune modulators, and new entries in existing classes of pharmacologic agents hold promise for the future (Hartman AF, Prim Care 1997;24(3):531–560). Because combination therapy with two, three, or more agents has become the standard of care, additive toxicities have become a major problem.

DISCLOSURE OF INVENTION

Applicants' invention rests on their finding that a select group of hypoestoxide analogs possess unexpected effectiveness as growth inhibiting agents against lentiviruses and against viruses of the family Herpetoviridae, including, respectively, HIV-1 and HSV-1 and HSV-2. In particular, the present invention comprises a method for inhibiting the growth of these viruses in subjects. The method comprises administering to a subject in need of antiviral therapy a pharmaceutical composition comprising a therapeutically effective amount of a compound of the formula

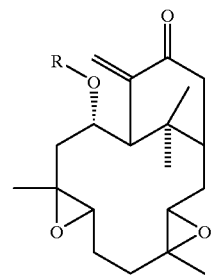

I where:
R is
(i) H, $PO_3^=$, alkyl of 1 to 12 carbon atoms substituted or unsubstituted, straight chain or branched, 0 to 6 double bonds, $(CH_2)_n$morpholine where n=1–4, morpholinomethylphenyl, orthoaminophenyl, orthohydroxyphenyl, $(CH_2)_n COOR_2$ where n=1–4 where $R_2$ is H, an alkalai metal salt, an alkaline earth metal salt, $NH_4^+$, $N^+(R_3)_4$
where $R_3$ is independently selected from the group consisting of H and alkyl of 1 to 4 carbon atoms, or
(ii) $COR_1$ wherein $R_1$ is selected from the group consisting of H, $(CH_2)_n CH_3$, where n=0–6, $(CH_2)_n COOR_2$ where n=1–4 and $R_2$ is previously defined, $(CH_2)_n N^+(R_3)_4$ wherein n=1–4, and $(CH_2)_n SO_3^-$ where n=1–4,
and pharmaceutically acceptable salts thereof.

In another aspect, the invention provides a method of treating a subject to alleviate pathological effects of the growth of viruses of the lentivirus family (e.g. HIV-1) and Herpetoviridae family (e.g. HSV-1 and HSV-2) in the subject. The method comprises administering to the subject at least one hypoestoxide having formula I. The hypoestoxide is administered to the subject in an amount sufficient to inhibit the growth of these viruses in said subject to thereby inhibit said effects.

BRIEF DESCRIPTION OF THE DRAWINGS

FIG. 2A shows the antiviral effect of JO-4 on Herpes simplex-1 (HSV-1) replication. Antiviral effects of JO-4 on HSV-1 were determined using Hybriwix Probe Systems: HSV antiviral susceptibility test kit from Diagnostic Hybrids, Inc. (Athens, Ohio).

FIG. 2B shows the antiviral effect of JO-4 on HSV-2 replication. Antiviral effects of JO-4 on HSV-2 were determined as described in FIG. 2A.

FIG. 2C shows the antiviral effect of JO-4A on HSV-2 replication. Antiviral effects of JO-4A on HSV-2 were determined as described in FIG. 2A.

MODES OF CARRYING OUT THE INVENTION

General Description and Definitions

Figure 1A:
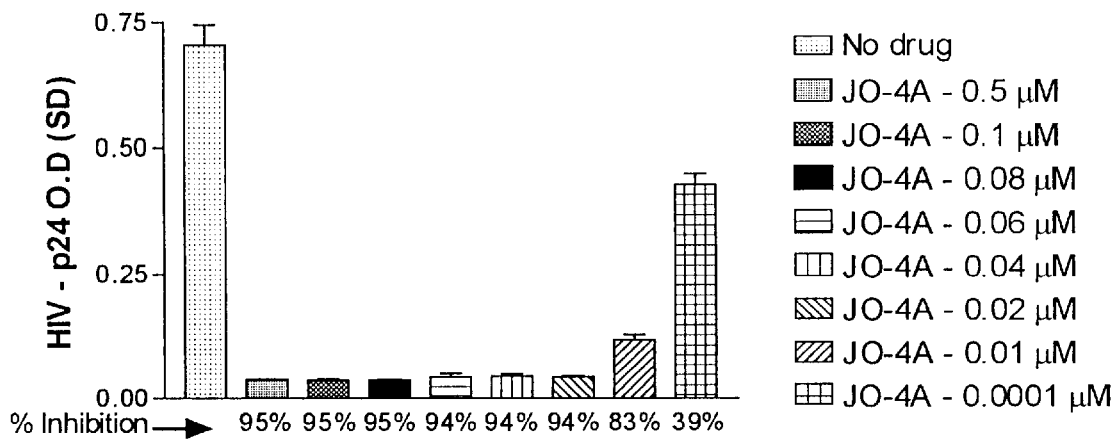
FIG. 1A shows the inhibitory effect of JO-4A on HIV-1 replication in cultured human peripheral blood mononuclear cells (PBMC). Human PBMCs were activated with PHA and infected with HIV-1 isolate from a patient. Infected PBMCs were cultured for 7 days either in the absence or presence of varying concentrations of JO-4A. (0.0001 μM–0.5 μM). At the end of culture, supernatants were collected and measured by ELISA for the presence of p24 antigen.

The practice of the present invention will employ, unless otherwise indicated, conventional molecular and cell biology, cell culture, biochemistry, and organic and medicinal chemical synthesis within the skill of the art. Such techniques are explained fully in the literature. See Bauer, D. J., *The Specific Treatment of Virus Diseases,* University Park Press, Baltimore, Md., 1977; Gadler, H., Nucleic Acid Hybridization for Measurement of Antiviral Compounds on Human Cytomegalvirus DNA Replication, *Antimicrobial Agents Chemotherap,* 1983, 24:370–374; Collier, L. H. and Oxford, J., eds., *Developments in Antiviral Therapy,* Academic Press, London, 1980; Coligan, J. E. et al., eds., *Current Protocols in Immunology,* 1993; Robert B. Belshe, ed., *Textbook of Human Virology,* 2nd. ed., 1991; Silverman, Richard B., The Organic Chemistry of Drug Design and Drug Action, Academic Press, Inc. NY (1992); Smith, Michael B., Organic Synthesis, McGraw Hill, Inc., NY, (1994)).

The following terminology will be used in accordance with the definitions set out below in describing the present invention.

The term "inhibiting the growth of" is used with respect to lentiviruses and Herpetoviridae viruses viruses that are pathological to human or other mammals. For example, with respect to the lentivirus HIV, "inhibiting the growth of" means inhibition of virus production as determined by decreased HIV $p^{24}$ levels in virus culture. Inhibiting the growth of HIV results on reduction of virus load, which, in turn, alleviates the pathological effects of HIV infection. It will be understood that as used herein, "inhibiting the growth of" effectively reduces viral load for a DNA or RNA virus of interest, which in turn, alleviates the pathological effects of infection by that DNA or RNA virus.

The term "pathological effects" as used herein is illustrated by an understanding of the life cycle of the lentivirus HIV and its effects in a host. It will be understood that lentiviruses include HIV-1, HIV-2, and HTLV, and that the method of the invention is directed for inhibiting the growth of HIV-1, HIV-2 or HTLV in subjects. The human immunodeficiency virus type 1 (HIV-1), a retrovirus, is a single-stranded RNA genome is packaged inside a protein core particle and surrounded by a lipid envelope in which is embedded the outer coat (envelope) protein, $gp^{120}$. Infection of T-helper (CD4$^+$) lymphocytes and monocytes begins with adsorption of virions to the cell surface mediated by the specific interaction of the virus envelope protein with CD4 molecules on the cell surface. After viral entry, the virus uncoats and the duplicate, single-stranded RNA genome is reverse-transcribed into a double-stranded DNA genome by the viral enzyme reverse transcriptase (RT). Integration into the host DNA is followed by transcription and translation of HIV-1 genes (*Arch. Intern. Med.,* 1997, 157:951–959).

Pathological/cytopathic effects of HIV consist, in part, of cell fusion with formation of syncitia and subsequent cell death (Belshe, R. B., ed., *Textbook of Human Virology,* 2nd ed., 1991), resulting in development of immunodeficiency. AIDS (acquired immunodeficiency syndrome) prestages include lymphadenopathy syndrome and the appearance of constitutional symptoms (AIDS-related complex or ARC). Lymphadenopathy syndrome is defined as enlargement of lymph nodes with any other recognizable cause other than HIV infection. Opportunistic infections comprise diseases with mostly ubiquitous parasites which are harmless in immunocompetent persons and acquire pathogenicity only in the presence of immunodeficiency. A high percentage of HIV-infected patients shows neurologic changes that are not explained by opportunistic infections or tumors. Dermatologic manifestations are frequently observed. Herpez zoster is an early clinical sign.

The family Herpetoviridae has several members which are widely disseminated human pathogens. These include herpes simplex virus (HSV), Epstein-Barr virus (EBV), cytomegalovirus (CMV), and varicella-zoster virus. It will be understood that the method of the invention is directed to inhibiting the growth herpetoviridae viruses including HSV-1 or -2, EBV, CMV and varicella-zoster. HSV, types 1 and 2, have been investigated in great detail at the molecular level because of their rapid replication cycle and high yields in tissue culture (Belshe, R. B., ed., *Textbook of Human Virology,* 2nd ed., 1991). In relation to HSV, the term "inhibiting the growth of " means inhibition of replication cycle, diminishing high yield or production of virus. Replication cycle involves: attachment, penetration, uncoating, early transcription, DNA replication, late transcription, and virus assembly. Pathological effects result from replication when host cells are infected. HSV infection alters cell organization at two levels, namely, changes in intracellular structures as well as in cell interactions. Cell protein and DNA synthesis are inhibited by viral protein(s). Chromosomes fragment during infection and remnants relocate to the inner surface of the nuclear membrane, thereby clearing the center of the the nucleus for viral replication. At a different level, interactions between cells are altered as a result of HSV infections in a manner influenced by viral strain or cell type or both. This is shown by varying degrees of aggregation of rounded cells and cell fusions. Cultured cells infected with variants of HSV often exhibit altered cell-cell associations, with increased clumping of syncytia formation.

Pathological effects of HSV type 1 result in Herpes simplex encephalitis (HSE), which is a life-threatening condition with high mortality and significant morbidity in survivors. Acute focal, necrotizing encephalitis including inflammation and swelling of the brain tissue with petechiae leading to larger hemorrhages are consistent features of the pathology of HSE (*Scand. J. Infect. Dis Suppl.* 100:8–13, 1996). Pathological effects of HSV 2 result in genital ulceration in developed countries. Herpesviruses, which are endemic in all human populations, include herpes simplex virus, varicella-zoster virus, EBV, CMV, and human herpesviruses-6, 7, and 8.

As used herein, the term "alleviate" means to lessen or reduce or make more bearable.

The term "subject" is taken to mean humans as well as other animals.

As used herein, the term "JO-4" means a compound which is a bicycle [9,3,1] pentadecane diterpene compound, as described in Z. Naturforsc 37 c: 558–561 (1982) and in Heterocycles 20:2125–2128 (1983), in which reference this compound is named "hypoestoxide." The chemical structure of JO-4 is illustrated in formula II.

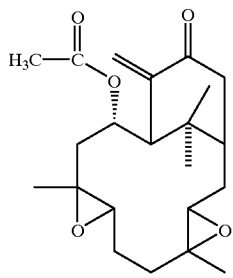

II

It is understood that the compounds illustrated in formula I include prodrugs of JO-4A. In terms of formula I, JO-4A is derived from JO-4 when R is H. The struture of JO-4A is illustrated in formula III

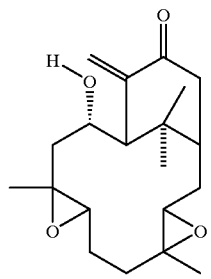

III

The term "prodrug," as used herein, refers to a pharmacologically inactive compound that is converted to an active drug by a metabolic transformation. (Silverman, Richard B. The Organic Chemistry of Drug Design, Acad. Press, 1992). There are numerous reasons why a prodrug strategy is used in drug design, the most common of which are to overcome problems associated with the compound, such as solubility, absorption and distribution, site specificity, instability, prolonged release, toxicity, poor patient acceptability, and formulation. Literature is available for guidance without undue experimentation for determining how to get compounds in pharmaceutical compositions to a locus to permit them to act, and guidance for how to obtain a therapeutically effective amount for inhibiting the growth of pathological RNA or DNA viruses, including but not limited to HIV or HSV, respectively, at the locus of action (McDonald, C. K., Kuritzkes, D. r., Human Immunodeficiency Virus Type 1 Protease Inhibitors, *Arch. Intern. Med.*, 1997, 157:951–959); Klagstaff, A. J., Faulds, D., Goa, K. L., Aciclovir: A Reappraisal of its Antiviral Activity, Pharmacokinetic Properties, and Therapeutic Efficacy, *Drugs*, 1994, 47(1):153–205; Hayashi, K., et. al., Characterization of Antiviral Activity of Sesquiterpene, triptofordin, *J. Antimicrob. Chemother.*, 1996, 37:759–768).

The most common prodrug form for drugs containing alcohol or carboxylic acid functional groups is an ester. Using skills well known in the art, it is possible to alter the structure of the compound to improve its pharmacokinetic properties and, thereby, transform it into a useful drug for therapeutic administration to an animal or human. JO-4 is a prodrug for JO-4A in the presence of serum esterases in the in vivo setting, and, in the in vitro setting if the culture medium contains added serum (which is most often the case). A preferred embodiment of the hypoestoxide compound for use in the method for inhibiting the growth of HIV or HSV in subjects to alleviate the pathological effects of the growth of HIV or HSV in subjects is the metabolite JO-4A, which is the free alcohol derivative of JO-4. JO-4 serves as an ester prodrug form for the delivery of JO-4A, which is formed over time after administration of JO-4 to cells or animals. In similar fashion, many other ester prodrugs of JO-4A provide delivery of JO-4A. Such prodrug forms and methods for making them are well known in the art, as cited above. These prodrugs are known to yield the parent drugs of interest upon exposure to esterases commonly found in serum of animals and humans. It is understood that the prodrugs of JO-4A useful in the claimed method yield JO-4A and are active in terms of inhibiting the growth of HIV or HSV.

The term "agonists" as used herein refers to substances that elicit the same response (i.e. inhibiting the growth of HIV or HSV in subjects in need of such treatment) as the compounds indicated in formula I. Agonists of the compounds of formula I include, but are not restricted to the prodrugs of JO-4A, which prodrugs are illustrated in formula I.

Methods for determining or screening modified forms of the hypoestoxide compounds i.e. prodrugs and/or agonists of the claimed compounds, for their ability to inhibit the growth of HIV or HSV in subjects in need of such treatment are well known in the art. (Belshe, R. B., ed., *Textbook of Human Virology*, 2nd ed., 1991).

The method of the present invention is directed to antiviral therapy, i.e. inhibiting the growth of lentiviruses or Herpetoviridae viruses in subjects using the compounds of formula I, and in particular, the compounds of formula II (JO-4A). The method of the present invention involves administering to a subject in need of such treatment a therapeutically effective amount of at least one hypoestoxide compound of formulas I. Preferred hypoestoxides for use in the method are JO-4 (formula II) and JO-4A (formula III). Another aspect of the method involves treating a subject to alleviate pathological effects of the growth of lentiviruses or Herpetoviridae viruses, such as HIV or HSV, respectively, in the subject. Pathological effects of HIV and HSV are well known in the art, and are described herein. It is also well understood that inhibiting the growth of HIV or HSV in a subject alleviates the pathology associated with these infections, as is well documented in the literature (Belshe, R. B., ed., *Textbook of Human Virology*, 2nd ed., 1991).

An embodiment of the method involves associating compounds of formulas I with a pharmaceutical carrier or diluent for administration to an subject.

Figure 1B:
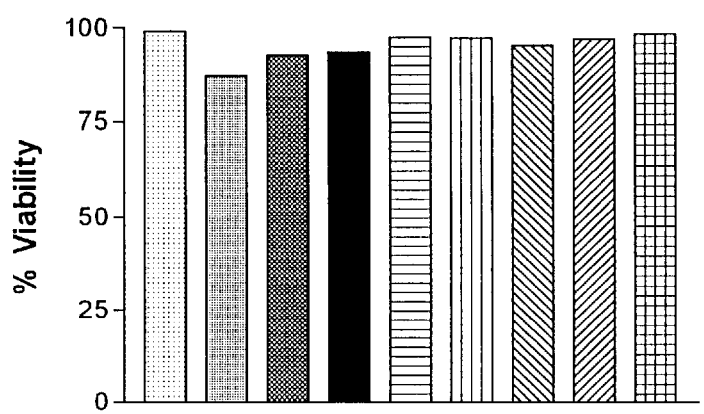
FIG. 1B shows the toxicity testing of JO-4A on cultured normal human PBMCs, which have been activated with PHA for 3 days. Activated PBMCs were cultured with 3% IL-2 for 7 days either in the absence or presence of varying concentrations of JO-4A. (0.0001 μM–0.5 μM). At the end of culture, the viability of the PBMCs were determined by trypan blue dye-exclusion test.

As detailed in the Examples below, administering JO-4A to HIV-1 infected PBMCs in vitro inhibited the growth of HIV-1, as illustrated in FIG. 1. At the same dosage level, JO-4A was not toxic to PBMCs (FIG. 1B). The growth-inhibiting effect of JO-4A on HSV-2 is illustrated in FIG. 2c.

For the above-mentioned use in subjects infected with lentivirus or Herpetoviridae viruses, for example, HIV or HSV, respectively, the therapeutic effective amount or dosage will, of course, vary depending on the compound employed, mode of administration and treatment desired. However, in general, satisfactory results would be obtained when administered orally or intraveneously at a daily dosage of from about 0.001 mg to about 1000 mg per kg animal body weight, conveniently given in divided doses 1 to 4 times a day or in sustained release form. If administered by injection, in general, satisfactory results would be obtained when administered at a daily dosage of from about 0.001 mg to about 200 mg per kg animal body weight, preferably in the range of from about 50 mg to about 200 mg per kg conveniently given in divided doses 1 to 4 times a day or in sustained release form. For the larger mammals, the total daily dosage would be in the range of from about 0.00 a to about 200 mg, and dosage forms suitable for oral administration comprise from about 0.001 mg to about 1000 mg of the compound admixed or in association with a solid or liquid pharmaceutical carrier or diluent. Methods are well known in the art for determining therapeutically effective amounts of the compounds used in the method of the invention. Such methods involve analysis of the pharmaceutical/pharmacokinetic parameters in antiviral therapy, i.e for inhibiting the growth of lentiviruses or Herpetoviridae viruses, for example, but not restricted to, HIV or HSV in subjects (Elion, G. B., Acyclovir: Discovery, Mechanism of Action, and Selectivity, *J. Med. Virol.* Suppl. 1:2–6, 1997; Wagstaff, A. J., et al., Drugs 1994, 47(1):153–205).

The method of the present invention includes administering a pharmaceutical composition comprising an effective amount of one or more of the compounds of formula I. Preferred embodiments are (JO-4A in pure form or as a pharmaceutically acceptable crude concentrate in association with a pharmaceutical carrier or diluent for HIV or HSV-2 infection; and JO-4 for HSV-1 or HSV-2 infection. Such compositions conveniently contain less than 1% by weight, and preferably about 0.2% by weight, of the compounds of formula I and may be prepared by conventional techniques to be in conventional forms, for example, capsules, tablets, suppositories, dispersible powders, syrups, elixirs, suspensions or solutions for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan monooleate, granulating and disintegrating agents such as starch and alginic acid, binding agents such as starch, gelatin and acacia and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period. Other compounds and methods known in the art for delaying disintegration or for timed-delayed or time-measured delivery of the active ingredients also find use in formulating the active ingredients for use in the methods of the invention. For example, the compounds of formula I may also be combined with liposomes or other delayed-release carrier means to protect the compounds from degradation until they reach their targets and/or facilitate movement of the compounds across tissue barriers.

The preferred compositions from the standpoint of ease of administration are solid compositions, particularly solid-filled gelatin capsules or tablets.

It is also to be understood that a further embodiment of the method of the invention involves combining one or more agents in a variety of protocols, including prophylaxis, with the method of the invention for administering to subjects in need of treatment for inhibiting the growth of lentiviruses or Herpetoviridae viruses or for alleviating the pathological effects of the growth of those viruses in a subject pharmaceutical compositions comprising compounds of formulas I. Combination protocols and methods for determining their efficacy, including therapeutic drug monitoring, are well known in the art (Belshe, R. B., ed., *Textbook of Human Virology*, 2nd ed., 1991). Examples of antiviral agents and other agents useful in therapy for inhibiting the growth of HIV or HSV which may be combined with administering the compounds of formulas I in the method of the invention include, but are not limited to famciclovir, aciclovir, valaciclovir, sorivudine (BV-arall), BW882C87, ganciclovir, brivudine, cidofovir (HPMPC), lobucavir, ISIS-2922, saqunavir, ritonavir, indinavir, nelfinavir (protease inhibitors); interferon-$\alpha/\beta$, azidothymidine (AZT, Retrovir, Zidovudine), dideoxycytidine (DDC), dideoxyadenosine, dideoxyinosine (DDI), ribavirin, peptide T, soluble recombinant CD4 receptor. Methods are well known in the art for determining therapeutically effective amounts of the compounds of formulas I and agents selected from the group of anti-viral agents or agents useful in anti-viral therapy in association with the compounds of formulas I in pharmaceutical compositions in the method of the invention.

The following materials and methods were employed in the non-limiting Examples set out below.

Peripheral Blood Mononuclear cells (PBMCs): Heparinized venous blood was obtained from healthy adult volunteers and PBMCs were separated by centrifugation over Ficoll-Hypaque (Pharmacia Biotech, Piscataway, N.J.). The cells were washed three times with HBSS (Hanks Balanced Salt Solution) and finally resuspended in RPMI-1640 medium (Mediatech, Inc., Herndon, Va.) supplemented with 20% fetal bovine serum (American Qualex, San Clemente, Calif.), 10 mM glutamine, 100 U/ml penicillin, and 100 $\mu$g/ml streptomycin (Sigma Chemicals, Saint Louis, Mo.) (complete medium). Cell viability was assessed by trypan blue dye exclusion test and the cell number was adjusted to required concentration.

Normal African green monkey kidney cells (CV-1): CV-1 cells from the Hybriwix™ Probe Systems: Herpes Antiviral Susceptibility Test kit (Diagnostic Hybrids, Inc., Athens, Ohio) were used for toxicity testing of JO-4A by MTT assay.

In Vitro HIV-1 Replication Assay: A standardized peripheral blood mononuclear cell culture assay for the determination of drug susceptibilities of clinical human HIV-1 isolates was utilized (Japour AJ et al. Antimicro Agents Chemother 1993; 37:1095–1101). Peripheral blood mononuclear cells ($2 \times 10^6$ cells/ml) were stimulated with PHA (5 $\mu$g/ml) in complete culture medium at 37° C., in a 5% $CO_2$-95% air-humidified incubator for 72 hours. The 3-day-old PHA-stimulated PBMC was sedimented at 400 g for 10 min at 20–24° C. Supernatant was removed and discarded. The cells were resuspended in complete culture medium supplemented with 3% IL-2. Cell viability was determined with 0.4% trypan blue. Viability was greater than 85%. Cell concentration was adjusted to $4 \times 10^6$/ml. Cells were dispensed in 50 $\mu$l volumes ($2 \times 10^5$/well) into 96 well microtiter plates containing 50 $\mu$l complete culture medium. HIV-1 infected cultures were initiated with a patient's HIV-1 isolate (50 $\mu$l/well) at a multiplicity of infection (MOI) of 0.05 and 0.1 respectively. JO-4A was added to wells in 50 $\mu$l volumes at varying concentrations (0.0001 $\mu$M–0.5 $\mu$M). The plates were incubated at 37° C. and 5% $CO_2$ in humidified chamber for 7 days. On day 4, half of the spent medium (100 $\mu$l) was discarded, and 50 $\mu$l of fresh complete medium and 50 $\mu$l of fresh JO-4A (varying concentrations as above) were added to wells containing spent JO-4A. 100 $\mu$l of fresh medium was added to wells without drug. On day 7, the culture was terminated and the supernatants were tested for HIV p24 antigen by an enzyme immunoassay (EIA) kit according to the recommendations of the manufacturer (Coulter™ HIV p24 Antigen Assay: Immunotech, Inc., Westbrook, Me.).

In Vitro Herpes simplex virus (HSV) (Type 1 and 2) Replication Assay: The antiviral activity of the drug was determined using the Hybriwix™ Probe Systems (Herpes Antiviral Susceptibility Test kit: Diagnostic Hybrids, Inc., Athens, Ohio). Briefly, either HSV-1 or HSV-2 isolates (ATTC, Rockville, Md.) were pre-adsorbed at 37° C. and 5% $CO_2$ in a humidified incubator for 60 minutes on African green monkey Kidney cells in a 24-well flat-bottom plate. Following pre-adsorption, the viral inoculum was removed and the growth medium containing various concentrations of appropriate drug was placed in appropriate wells. The culture was continued for 48 hours for the amplification of the virus. Quantification of the HSV DNA present in each well was determined by the nucleic acid hybridization method. The cells and/or virus were lysed with DNA wicking agent and the single-stranded DNA was immobilized on a Hybriwix™ filter by a vertical capillary absorption of the wicking agent/DNA solution. The amount of HSV target DNA from each well was determined using radioactive ($I^{125}$)-HSV DNA probe containing genetic sequences, which are homologous to HSV-1 or HSV-2 sequences. The amount of radioactivity present on the Hybriwix™ was dependent upon the amount of HSV DNA present after culture, and was determined in a gamma counter (Packard Instrument Co., Meriden, Conn.).

Colorimetric MTT assay: Cytotoxic effects of drugs were determined in vitro by a colorimetric assay (Mosmann, T., J. *Immunol. Methods*, 65: 55–63, 1983). Briefly, 1000 cells per well (100 μl) in a 96-well flat-bottom plate were cultured either with the culture medium alone or with various concentrations of drug at 37° C., in a 5% $CO_2$-95% air humidified incubator for 72 hours. At the end of the culture, 10 μl of 5 mg/ml sterile solution of 3-(4,5-Dimethylthiazol-2yl)-2,5-diphenyltetrazolium bromide (MTT) (Sigma Chemicals, Saint Louis, Mo.) in PBS was added per well and the incubation was resumed for an additional 4 hours. Acid-isopropanol (100 μl of 0.04 N HCl in isopropanol) was added to all wells and kept at room temperature for 30 minutes. Mixing with a multichannel pipetter dissolved the dark blue crystals and the absorbance was measured at 545–650 nm using an ELISA plate reader.

COMPOUNDS USED IN THE METHOD

Hypoestoxide compounds (formula I) tested in the method of the invention included JO-4A (formula III), JO-4 (formula II), which is an ester of JO-4A.

COMPOUND PREPARATION

Preparation of JO-4A (Formula III). JO-4 crystals (82 mg, 0.22 mmol) were dissolved in a mixture of methanol (3 mL) and dioxane (3 mL) with warming and then cooled to room temperature. Fresh sodium methoxide powder was added to "pH 10". The mixture was stirred at room temperature overnight and the clear, orange-yellow reaction mixture was neutralized with Dowex -50 H+ resin, filtered and evaporated in vacuo to yield a pale yellow syrup which slowly crystallized in the freezer overnight. Yield 65 mg, 90%.

Preparation of JO-4B (formula IV). (Method of E. J. Corey and G. Schmidt, *Tetrahedron Letters*, 399–402, 1979.) JO-4A (50 mg, 0.15 mmol) was dissolved in dichloromethane (1 mL) and cooled to 0° C. and 1.5 molar equivalents of pyridinium dichromate was added with efficient stirring. The reaction mixture was allowed to stir at room temperature for 6 hours and then diluted with ether, filtered and evaporated to yield an off-white solid (30 mg, 60%).

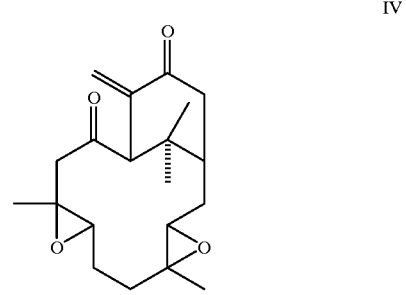

IV

Esters of JO-4. As shown in formula I, the compounds used in the method of the invention comprise esters of JO-4A (formula III), including JO-4 (formula II), which was disclosed in Heterocycles 20:212502128 (1983) and in Z. *Naturoorsch* 37c:558–561 (1982).

Accordingly, the method of the invention comprises administering to subjects a therapeutically effective amount of at least one hypoestoxide compound having formula I

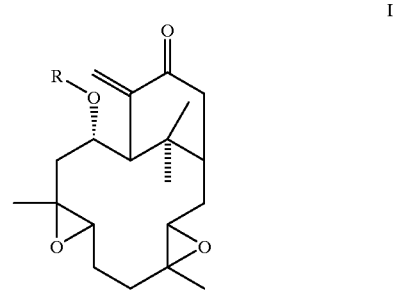

I in which

R is

H, $PO_3^=$, alkyl of 1 to 12 carbon atoms substituted or unsubstituted, straight chain or branched, 0 to 6 double bonds, $(CH_2)_n$morpholine where n=1–4, morpholinomethylphenyl, orthoaminophenyl, orthohydroxyphenyl, $(CH_2)_n COOR_2$ where n=1–4 where $R_2$ is H, an alkalai metal salt, an alkaline earth metal salt, $NH_4^+$, $N^+(R_3)_4$ where $R_3$ is independently selected from the group consisting of H and alkyl of 1 to 4 carbon atoms, $COR_1$ wherein $R_1$ is selected from the group consisting of H, $(CH_2)_n CH_3$, where n=0–6, $(CH_2)_n COOR_2$ where n=1–4 and $R_2$ is previously defined, $(CH_2)_n N^+(R_3)_4$ wherein n=1–4, and $(CH_2)_n SO_3^-$ where N=1–4, and pharmaceutically acceptable salts thereof. A preferred embodiment of the method of the invention administers pharmaceutical compositions comprising a therapeutically effective amount of the compound of formula III (JO-4A) for inhibiting the growth of HIV and HSV-2. Another preferred embodiment of the method of the invention administers pharmaceutical compositions comprising a therapeutically effective amount of the compound of formula II (JO-4) for inhibiting the growth of HSV-1 or IV and HSV-2.

Isolation of JO-4 from *Hypoestes rosea*.

The general procedure for isolation of pure JO-4 (formula II) from dried *Hypoestes rosea* plant material involved solid/liquid extraction using boiling hexanes in a large Soxhlet apparatus. *Hypoestes rosea* is a shrub of the family Acantheceae. (Okugun, J. I. et al., Z. Naturforsch 37c:558–561 (1982)) The crude extract obtained from the hexanes upon evaporation was subjected to flash silica gel column chromatography using a step gradient solvent system beginning with petroleum ether (30–60 bp) and stepping to 5% ethyl acetate, then to 10% and then 20%. At 30% ethyl acetate JO-4 was eluted from the column. The appropriate fractions were combined and concentrated to dryness, and petroleum ether or hexanes was added to obtain crystalline JO-4. One such procedure provided 240 mg pure JO-4 from 10 g crude extract from leaves.

Important notes: The crude extract was first dissolved in a minimum of ethyl acetate and absorbed onto silica gel and evaporated to a dry powder before loading onto the column, prepacked in petroleum ether. Extraction of specific parts of the plant indicated that the leaves were the structures that contained the majority of the JO-4 as opposed to the stems.

As shown in the Examples below, the compounds of formulas II (JO-4) and III (JO-4A) were found to have unexpected effectiveness as agents for inhibiting the growth of, respectively, HSV1 and HSV2, and of HIV and HSV-2 as shown by their effects on viral growth as indicated in standard in vitro predictive of a compound's anti-viral activity in vivo in humans or other animals.

The compound of formula II (JO-4) as demonstrated herein, inhibited the replication and growth of HSV-1 and HSV-2 in African Green Monkey kidney cells, a screening test well known in the art for predicting anti-HSV-1 or anti-HSV-2 activity in a subject, and from which one of reasonable skill in the art would consider JO-4 useful in a method for inhibiting the growth of HSV-1 or HSV-2 in subjects in need of anti-viral therapy, thereby alleviating the pathological effects of HSV-1 or HSV-2 infection.

The compound of formula III (JO-4A as demonstrated herein, inhibited the replication and growth of HIV in human PBMCs and HSV-2 in African Green Monkey kidney cells, screening tests well known in the art for predicting anti-HIV or anti-HSV-2 activity, respectively, in a subject, and from which one of reasonable skill in the art would consider JO-4A useful in a method for inhibiting the growth of HIV or HSV-2 in subjects in need of anti-viral therapy, thereby alleviating the pathological effects of HIV or HSV-2 infection, respectively.

It was found that the medicinal activity of the compounds of formula I—in particular JO-4 and JO-4A, for inhibiting the growth of HIV or HSV in the in vitro tests reported below formed the basis for the inventors' conclusions that the compounds, and that the pharmaceutical compositions comprising them have in vivo efficacy in the inhibition of growth of HIV or HSV in an animal or human host.

EXAMPLES

Example 1

Anti-Viral Effect of JO-4A on HIV Growth in PBMCs

FIG. 1A is representative of results from several experiments on the inhibitory effects of JO-4A on HIV-1 isolate from a patient. The results demonstrate that JO-4A has the dose dependent inhibitory effect on HIV-1 replication and it was concluded that the inhibitory concentration $_{50}$(IC$_{50}$), i.e., the drug concentration capable of inhibiting 50%, was between 0.0001 $\mu$M and 0.01 $\mu$M.

FIG. 1B shows the toxicity testing results of JO-4A on cultured human PBMC by trypan blue dye-exclusion test. JO-4A has no toxic effect at any of the concentrations tested. Therefore, the inhibitory effect on HIV-1 replication by JO-4A is not due to cytotoxicity of JO-4A on PBMCs.

Example 2

Anti-Viral Effect of JO-4 on HSV-1 and HSV-2 Growth

FIG. 2A shows the antiviral effect of JO-4 on HSV-1 replication. Following two days of culture with various concentrations of JO-4, HSV-1 replication in African green monkey kidney cells was inhibited by 60% with 12.5 $\mu$M and 53% with 3.125 $\mu$M. Thus, the IC$_{50}$ dose for JO-4 on HSV-1 inhibition was determined to be ~3.125 $\mu$M.

FIG. 2B shows the antiviral effect of JO-4 on HSV-2 replication. After two days of culture with various concentrations of JO-4, HSV-2 replication in African green monkey kidney cells was inhibited by 65% with 12.5 $\mu$M and 58% with 3.125 $\mu$M. The IC$_{50}$ dose for JO-4 on HSV-1 inhibition was determined to be <3.125 $\mu$M.

FIG. 2C shows the antiviral effect of JO-4A on HSV-2 replication. After two days of culture with various concentrations of JO-4A, HSV-2 replication in African green monkey kidney cells was inhibited by 61% with 12.5, $\mu$M, 51% with 3.125 $\mu$M and 20% with 0.75 $\mu$M. The IC$_{50}$ dose for JO-4A on HSV-2 inhibition was determined to be ~3.125 $\mu$M.

Example 3

Toxicity Study of JO-4 and JO-4A on Cultured Cells

Figure 3A:
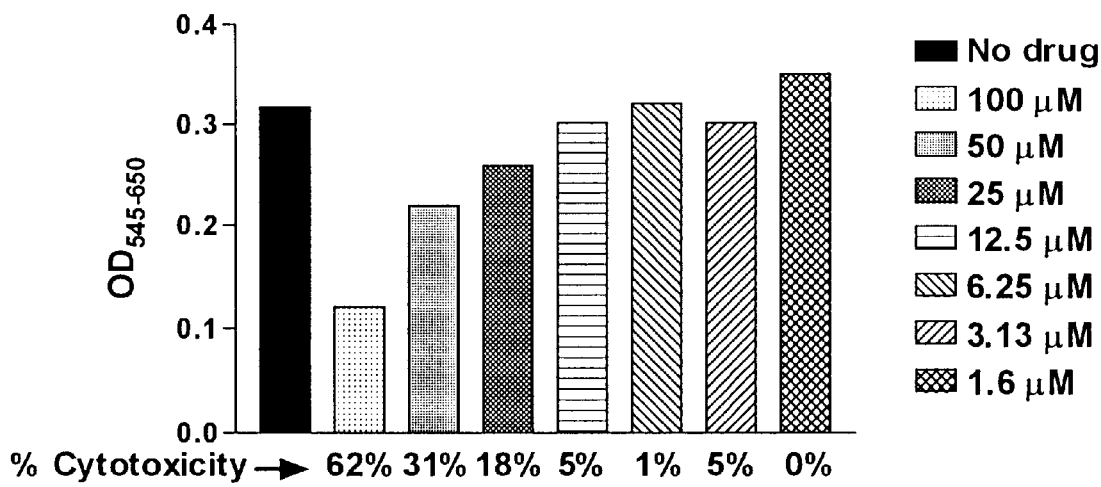
FIGS. 3A and 3B show the results of toxicity testing of JO-4 and JO-4A on normal, uninfected African green monkey kidney cells (CV-1), respectively. CV-1 cells were cultured either in the presence or absence of various concentrations of drugs for 72 hours. Cytotoxicity was determined by colorimetric (MTT) assay.
Figure 3B:
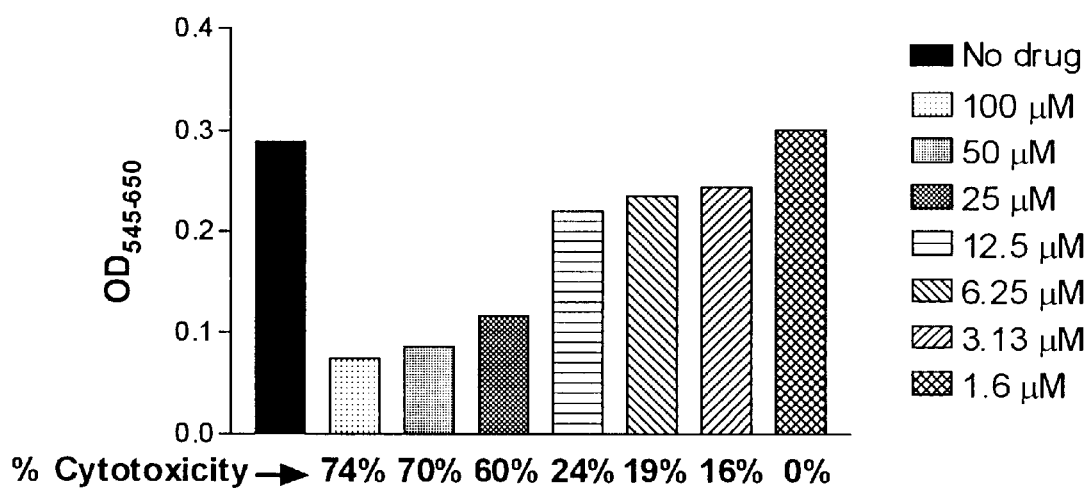

FIGS. 3A and 3B show the results of toxicity testing of JO-4 and JO-4A on normal, uninfected African green monkey kidney cells (CV-1). When CV-1 cells were cultured either in the presence or absence of various concentrations of JO-4 and JO-4A for 72 hours, cytotoxicity of greater than 50% was obtained only at higher concentrations of the compounds (>50 $\mu$M for JO-4; and ~25 $\mu$M for JO-4A). Therefore, the inhibitory effect of JO-4 and JO-4A on HSV-1 and HSV-2 replication was not due to the cytotoxicity of the respective drugs against CV-1 cells.

Modifications of the modes for carrying out the invention described above that are obvious to those of skill in the chmical, biochemical, pharmaceutical and/or medical arts are intended to be within the scope of the following claims:

What is claimed is:

1. A method for inhibiting the growth of viruses and/or virus infected cells, including but not limited to lentiviruses or Herpetoviridae viruses in subjects, which viruses and/or virus infected cells are sensitive to compounds, selected from the group consisting of at least one hypoestoxide having a formula as follows:

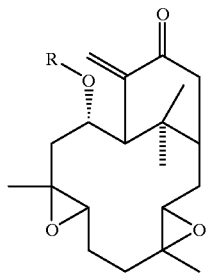

I

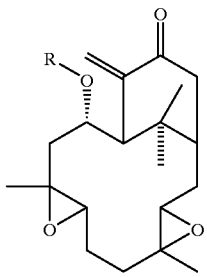

I where

R is H, $PO_3^=$, alkyl of 1 to 12 carbon atoms substituted or unsubstituted, straight chain or branched, 0 to 6 double bonds, $(CH_2)_n$morpholine where n=1–4, morpholinomethylphenyl, orthoaminophenyl, orthohydroxyphenyl, $(CH_2)_n COOR_2$ where n=1–4
where $R_2$ is H, an alkalai metal salt, an alkaline earth metal salt, $NH_4^+$, $N^+(R_3)_4$ where $R_3$ is independently selected from the group consisting of H and alkyl of 1 to 4 carbon atoms, $COR_1$ wherein $R_1$ is selected from the group consisting of H, $(CH_2)_n CH_3$, where n=0–6, $(CH_2)_n COOR_2$ where n=1–4 and $R_2$ is previously defined, $(CH_2)_n N^+(R_3)_4$ wherein n=1–4, and $(CH_2)_n SO_3^-$ where N=1–4, and pharmaceutically acceptable salts thereof.

2. The method of claim 1 wherein R is H.

3. The method of claim 1 wherein said lentivirus is selected from the group consisiting of HIV-1, HIV-2, and HTLV.

4. The method of claim 1 wherein said Herpetoviridae virus is selected from the group consisting of herpes simplex virus, Epstein-Barr virus, cytomegalovirus, and varicella-zoster virus.

5. A method of treating a subject to alleviate pathological effects of the growth of lentivirus or Herpetoviridae virus in a subject, wherein the method comprises administering to the subject at least one hypoestoxide having the formula:

where

R is H, $PO_3^=$, alkyl of 1 to 12 carbon atoms substituted or unsubstituted, straight chain or branched, 0 to 6 double bonds, $(CH_2)_n$morpholine where n=1–4, morpholinomethylphenyl, orthoaminophenyl, orthohydroxyphenyl, $(CH_2)_n COOR_2$ where n=1–4
where $R_2$ is H, an alkali metal salt, an alkaline earth metal salt, $NH_4^+$, $N^+(R_3)_4$ where $R_3$ is independently selected from the group consisting of H and alkyl of 1 to 4 carbon atoms, $COR_1$ wherein $R_1$ is selected from the group consisting of H, $(CH_2)_n CH_3$, where n=0–6, $(CH_2)_n COOR_2$ where n=1–4 and $R_2$ is previously defined, $(CH_2)_n N^+(R_3)_4$ wherein n=1–4, and $(CH_2)_n SO_3^-$ where N=1–4, and pharmaceutically acceptable salts thereof wherein said hypoestoxide is administered to said subject in an amount sufficient to inhibit the growth of lentivirus or Herpetoviridae in said subject to thereby alleviate said effects.

6. The method of claim 5 wherein R is H.

7. The method of claim 5 wherein said lentivirus is selected from the group consisiting of HIV-1, HIV-2, and HTLV.

8. The method of claim 5 wherein said Herpetoviridae virus is selected from the group consisting of herpes simplex virus, Epstein-Barr virus, cytomegalovirus, and varicella-zoster virus.

* * * * *